United States Patent
Geuder (10) Patent No.: US 9,668,918 B2
(45) Date of Patent: Jun. 6, 2017

(54) APPARATUS FOR CUTTING AND ASPIRATING TISSUE

(76) Inventor: Volker Geuder, Heidelberg (DE)

( * ) Notice: Subject to any disclaimer, the term of this patent is extended or adjusted under 35 U.S.C. 154(b) by 97 days.

(21) Appl. No.: 13/880,353

(22) PCT Filed: Oct. 11, 2011

(86) PCT No.: PCT/DE2011/050043
§ 371 (c)(1),
(2), (4) Date: Apr. 18, 2013

(87) PCT Pub. No.: WO2012/059092
PCT Pub. Date: May 10, 2012

(65) Prior Publication Data
US 2013/0211439 A1    Aug. 15, 2013

(30) Foreign Application Priority Data
Nov. 5, 2010   (DE) .................. 10 2010 050 337

(51) Int. Cl.
*A61F 9/007*   (2006.01)
*A61B 17/32*   (2006.01)
*A61B 10/02*   (2006.01)

(52) U.S. Cl.
CPC .... *A61F 9/00763* (2013.01); *A61B 17/32002* (2013.01); *A61B 10/0275* (2013.01);
(Continued)

(58) Field of Classification Search
CPC .. A61B 17/32002; A61B 2017/320028; A61B 2017/32004; A61F 9/00763; A61F 9/00736
(Continued)

(56) References Cited

U.S. PATENT DOCUMENTS

| 4,811,734 A | 3/1989 | McGurk-Burleson et al. |
| 5,106,364 A | 4/1992 | Hayafuji et al. |

(Continued)

FOREIGN PATENT DOCUMENTS

| DE | 10032007 A1 | 1/2002 |
| WO | WO 98/46147 A1 | 10/1998 |
| WO | WO 98/52502 A1 | 11/1998 |

OTHER PUBLICATIONS

International Searching Authority, International Search Report for International Application No. PCT/DE2011/050043, mailed Mar. 30, 2012, European Patent Office, The Netherlands.
(Continued)

*Primary Examiner* — Anh Dang
(74) *Attorney, Agent, or Firm* — Alston & Bird LLP (57) ABSTRACT

An apparatus for cutting and aspirating tissue from the human body or animal body, particularly for application in vitrectomies, for retinal detachment, etc., having an outer tube (1) and an inner tube (5) which can slide back and forth concentrically in the outer tube (1) with minimal play, wherein the outer tube (1) is closed on the free end (2) thereof, and has a lateral opening (3) near the free end (2), with at least one inner cutting edge (4), wherein the inner tube (5) is open on the free end and has an outer cutting edge (6) at that position, and wherein the cutting edges (4, 6) work together in a cutting manner when the inner tube (5) is displaced, characterized in that the inner tube (5) has at least one lateral opening (7) with at least one further outer cutting edge (8) near the free end.

19 Claims, 7 Drawing Sheets

(52) U.S. Cl.
CPC .............. *A61B 2017/320028* (2013.01); *A61B 2217/005* (2013.01)

(58) Field of Classification Search
USPC ........ 606/107, 167, 170, 171; 600/564, 566, 600/567, 571
See application file for complete search history.

(56) References Cited

U.S. PATENT DOCUMENTS

| | | | |
|---|---|---|---|
| 5,423,844 A | | 6/1995 | Miller |
| 5,474,532 A | | 12/1995 | Steppe |
| 5,630,827 A | | 5/1997 | Vijfvinkel |
| 5,980,546 A | | 11/1999 | Hood |
| 6,156,049 A | * | 12/2000 | Lovato .................. A61B 1/015 604/22 |
| 2010/0106054 A1 | | 4/2010 | Hangai et al. |

OTHER PUBLICATIONS

International Searching Authority, Written Opinion for International Application No. PCT/DE2011/050043, mailed Mar. 30, 2012, European Patent Office, Germany.
The International Bureau of WIPO, International Preliminary Report of Patentability (English Translation of Written Opinion) for International Application No. PCT/DE2011/050043, mailed May 8, 2013, 7 pages, Switzerland.

\* cited by examiner

Fig. 2

APPARATUS FOR CUTTING AND ASPIRATING TISSUE

CROSS REFERENCE TO RELATED APPLICATIONS

This application is a national stage application, filed under 35 U.S.C. §371, of International Application No. PCT/DE2011/050043, filed Oct. 11, 2011, which claims priority to and the benefit of German Application No. 10 2010 050 337.1, filed Nov. 5, 2010, the contents of both of which are hereby incorporated by reference in their entirety.

BACKGROUND

Technical Field

The invention relates to a device for the cutting and suctioning of tissue from the human body or animal body, particularly for application in vitrectomies, in cases of retinal detachment, etc. The device includes an outer tube and an inner tube which can slide concentrically inside the outer tube in both directions with minimal play, wherein the outer tube is closed on the free end thereof, and has a lateral opening with at least one inner cutting edge near the free end. The inner tube is open on the free end and has an outer cutting edge at this position. The cutting edges work together with a cutting function when the inner tube is slid.

In principle, the invention relates to a surgical cutting instrument for the removal of tissue. By means of the instrument, it is possible to cut tissue on and/or in the body and suction out the same from and/or off of the body. Concretely, the invention can relate to a very special cutting instrument by means of which it is possible to destroy and/or break up the vitreous humor in the eye, and remove the same from the eye, as part of a vitrectomy. In addition, it is possible to remove blood, coagulated blood, and connective-tissue-like alterations and regions of the retina resulting from retinal peeling by using this instrument.

Description of Related Art

By way of example for prior art, reference is made only to U.S. Pat. No. 5,630,827, in which a cutting instrument suitable for vitreous humor operations is known. The cutting device is open on the proximal end. On the distal end [thereof], it has a closed outer sheath which has multiple openings near the closed end. The openings each form a slot and enable vitreous humor tissue to penetrate into the lumen of the outer sheath. In addition, the cutting instrument has an inner sheath which is arranged concentrically to the outer sheath, and which is accommodated in the outer sheath in a manner allowing longitudinal movement, and which has a sharp edge on its distal end for the purpose of cutting the vitreous humor when the inner sheath is slid forward.

In the case of the device known from U.S. Pat. No. 5,630,827, it is essential that the inner tube has an open, peripheral edge on its free frontal end which serves as the cutting edge. This edge is accordingly shaped and/or sharpened. The outer edge region bears the cutting function, and consequently from this point forward, the document discusses an outer cutting edge of the inner tube. This outer cutting edge works together with one or more inner cutting edges of the outer tube, such that tissue which has pressed into the device is cut and/or separated upon the cutting edges mutually sliding past each other. Next, the tissue can be suctioned out of the interior of the device—more precisely stated, through the inner tube.

A cutting instrument characteristic of the class is likewise known from WO 98/52502, for the purpose of removing vitreous humor tissue. A closed outer sheath is included at the distal end of the instrument, and has multiple slits near the distal end through which the vitreous humor tissue can enter. An inner sheath is included concentric to the outer sheath, and can move longitudinally, having a sharp edge on its distal end for cutting the vitreous humor tissues which have penetrated into the tube. In addition, a drive mechanism is included for the inner sheath, by means of which it is possible to move the inner sheath with its cutting edge in the region of the distal end past the slit arranged in the outer sheath, such that a cutting process is realized at this point in both directions.

However, the known devices of the type which characterizes the class are problematic in practice for two reasons. First, the work speed [with the instrument] is limited by the frequency with which the inner tube is moved back and forth, particularly with its outer cutting edge moving past the inner—or the inner cutting edge moving past the outer—tube. As such, only a certain amount of tissue can be cut with each stroke of the inner tube, whereby the throughput is limited by the maximum frequency.

In addition, it is disadvantageous that the known device generates very significant pressure and/or vacuum fluctuations in the eye, particularly as a result of the fact that the opening or openings which serve to provide suctioning is/are alternatingly completely closed and completely open according to the position of the inner tube. As a result, an alternating vacuum is created in the body and/or eye which is essentially impossible to compensate. The resulting significant pressure fluctuations can lead to damage to the eye.

BRIEF SUMMARY

Therefore, the present invention addresses the problem of designing and implementing the device, which characterizes the class, for cutting and suctioning tissue from the human body or animal body, particularly for application in vitrectomy, in such a manner that it is possible to realize significant cutting performance and therefore high throughput without increasing the frequency for the back and forth movement of the inner tube, while at the same time preventing pressure fluctuations in the body to the greatest possible extent.

The problem above is addressed by the features of claim 1. According to the claim, the device which characterizes the class is characterized in that the inner tube has at least one lateral opening near the free end, with at least one further outer cutting edge.

According to the invention, it has been recognized that it is very significantly advantageous, as concerns cutting performance, if the inner tube has at least one further cutting edge which works together with the cutting edge or the cutting edges of the outer tube. This can be realized in an amazingly simple manner by a configuration wherein the inner tube has at least one lateral opening near the free end, similarly to the outer tube. This lateral opening in the inner tube has at least one further outer cutting edge, such that the inner tube is equipped with a total of at least two cutting edges. As such, during the stroke of the inner tube, the frontal cutting edge thereof—meaning the cutting edge on the free end of the inner tube—and the at least one further cutting edge, move past the inner cutting edge of the outer tube, such that assuming the construction presented above, at least two cuts are made per stroke.

Given the assumption that the lateral opening of the inner tube, for example in the form of a slit designed along the lines of a ring segment, is equipped with two additional outer cutting edges, the inner tube can have two outer cutting edges in the lateral opening, and can have the frontal cutting edge, meaning a total of three outer cutting edges, such that three cuts are made upon every back and forth movement of the inner tube—specifically two cuts with the forward movement, and at least one cut with a backward movement of the inner tube.

In any case, it is essential according to the invention that the inner tube can have at least one, and by all means two or more lateral openings near the free end, which are equipped with a total of three or four outer cutting edges. In a configuration having three openings, these can be equipped with up to six additional cutting edges [sic].

In a further advantageous manner, the openings in the inner tube are designed as slits constructed parallel to each other and having parallel cutting edges positioned opposite each other. Numerous other embodiments can be contemplated, including, by way of example, oval openings with cutting edges curved accordingly.

However, it is possible to increase the cutting performance further, particularly by means of a further constructive measure whereby the outer tube has two neighboring openings near to the free, closed end, equipped with a total of three or four inner cutting edges. The cutting edges work together with the additional cutting edges of the inner tube, such that more cutting motions result overall according to the number of the cutting edges sliding past each other, and specifically with each partial stroke.

The openings designed in the outer tube can be designed as slits which are parallel to each other and which have parallel cutting edges, like the openings in the inner tube. In this case as well, it can be contemplated that the openings are included in different sizes and with different shapes, for example a lens shape and/or oval. Accordingly, the cutting edges can be designed to run around the periphery, such that they work like two differently oriented cutting edges with respect to the forward stroke and the backward stroke.

In principle, it can be contemplated that the cutting edges run transverse to the longitudinal axis of the tubes. It can likewise be contemplated that the cutting edges run diagonally to the longitudinal axis of the tubes, or are even arranged with an offset to each other in the longitudinal direction.

In a further variant, it can be contemplated that the cutting edges of the inner tube have a different angle with respect to the longitudinal axis than the cutting edges of the outer tube. As such, the stroke movement of the inner tube results in a type of scissor effect with respect to the cutting edges sliding by each other. This further enhances the cutting performance.

In principle, the cutting edges can be designed as straight, curved, wavy, or even crooked in order to achieve a special cutting effect, particularly with respect to the tissue being cut.

It can also be contemplated that the openings which extend inward into the respective tubes run orthogonally to the longitudinal axis of the tubes. It is also possible that the openings and/or slits are inclined inward toward the free end of the tube or away from the free end of the tube, meaning at a degree other than 90°.

As already mentioned above, the outer tube has inner cutting edges, and the inner tube has outer cutting edges, wherein the cutting edges of each slide past each other when the inner tube executes a stroke, thereby producing the cutting effect both upon the forward stroke and the backward stroke. Defined cutting surfaces extend from the cutting edges as a result of the material thickness of the tubes, and specifically in each case falling away outward from the cutting edge (in the case of the outer tube) and/or inward (in the case of the inner tube). As such, it is possible to define each cutting edge via the cutting surface, and also optionally sharpen and/or machine finish the same.

The openings and/or slits of each tube are fundamentally spaced apart from each other in the axial dimension. It can also be contemplated that multiple openings or slits are arranged offset to each other around the periphery in order to produce a cutting effect, particularly around the periphery of the device. According to requirements, it is possible to realize numerous different arrangements, including the nesting of openings, beyond just the periphery of each tube.

With respect to preventing pressure fluctuations in the body, it is particularly very advantageous if the device is constructed on the basis of a simple constructive measure using simple control technology, in such a manner that no pressure fluctuations occur during operation in any body, even though each opening, when considered in isolation, is covered differently by the inner tube. In a more refined manner, it can be contemplated that the openings and therefore the cutting edges of the tubes are arranged with respect to each other over the entire movement process of the inner tube in such a manner that the openings are sized in such a manner—and that the movement of the inner tube is limited and/or controlled in such a manner—that at every point in time of the movement process, meaning over the entire forward stroke and backward stroke of the inner tube, the same cross-section for flow into the inner tube is present. This means that, by way of example, a frontal opening in the outer tube is completely opened while a second rear opening in the outer tube is completely closed by the inner tube. During the backward stroke of the inner tube, the frontal opening is gradually closed, particularly to the same degree as the rear opening of the outer tube is opened by the backward stroke of the inner tube. Regardless of the number of the openings, it is possible given a corresponding construction to design the arrangement of the outer tube and the inner tube and the openings and/or slit included in the same in such a manner that the requirement presented above is complied with at all times, such that particularly at every point in time of the movement process, meaning over the entire forward stroke and backward stroke of the inner tube, the effective cross-section of flow through all openings is the same, such that over the entire movement process, no pressure fluctuations are produced due to the vacuum which is required for the suctioning and which is present in the interior of the device. In contrast, the vacuum and/or suction which acts on the exterior always stays the same, such that the configuration rules out possible damage to the eye as a result of pressure fluctuations, particularly while preventing corresponding pressure fluctuations which act on the exterior.

DETAILED DESCRIPTION OF THE DRAWINGS

At this point, there are various possibilities to embody and implement the teaching of the present invention in an advantageous manner. On this, reference is made to the dependent claims following claim 1, as well as to the following explanation of a preferred embodiment of the invention and the associated illustration. Along with the explanation of the preferred embodiment of the invention with reference to the illustration, preferred embodiments and implementations of the teaching are also explained in general. In the illustrations:

DETAILED DESCRIPTION OF VARIOUS EMBODIMENTS

FIGS. 1 to 6 show highly enlarged schematic views of the working region of the device according to the invention, wherein the same is a so-called vitrector for application in vitrectomies, particularly a device for the removal of vitreous humor from the human eye.

Together, FIGS. 1 to 6 show the movement profile and the positions of the moving parts relative to each other.

More concretely, FIGS. 1 to 6 partially show the outer tube 1 which is closed on the free end 2. In the embodiment shown in FIGS. 1 to 6, the outer tube 1 is equipped with a total of two openings 3 which are designed in the shape of symmetrical slits. Due to the disposition of the two openings 3, the outer tube 1 has a total of four cutting edges 4.

An inner tube 5 is arranged concentrically inside of the outer tube 1, with minimal play, and is able to slide back and forth. It is possible to see in FIGS. 1 to 6 that the inner tube 5 is open on its frontal free end. Accordingly, a first cutting edge 6 is constructed at this position. According to the direction of the stroke of the inner tube 5, the cutting edge 6 cuts each time when it slides past a cutting edge 4 oriented opposite the direction of movement of the inner tube 5. Therefore, in the embodiment shown in FIGS. 1 to 6, the cutting edge 6 cuts a maximum of two times, particularly as it is guided past each of the cutting edges 4 of the outer tube 1, said cutting edges [4] oriented opposite [the cutting edge 6], with the stroke in the corresponding direction.

At this point, the inner tube 5 can be equipped with one or with two openings 7 which likewise are designed in the form of a slot. The openings 7 of the inner tube 5 can have approximately the same degree of opening as the openings 3 of the outer tube 1.

The provision of an opening 7 can involve the same having two additional outer cutting edges 8 which realize a cutting process upon sliding by a cutting edge 4 of the outer tube 1, said cutting edge [4] being oriented in the opposite direction.

Figure 1:
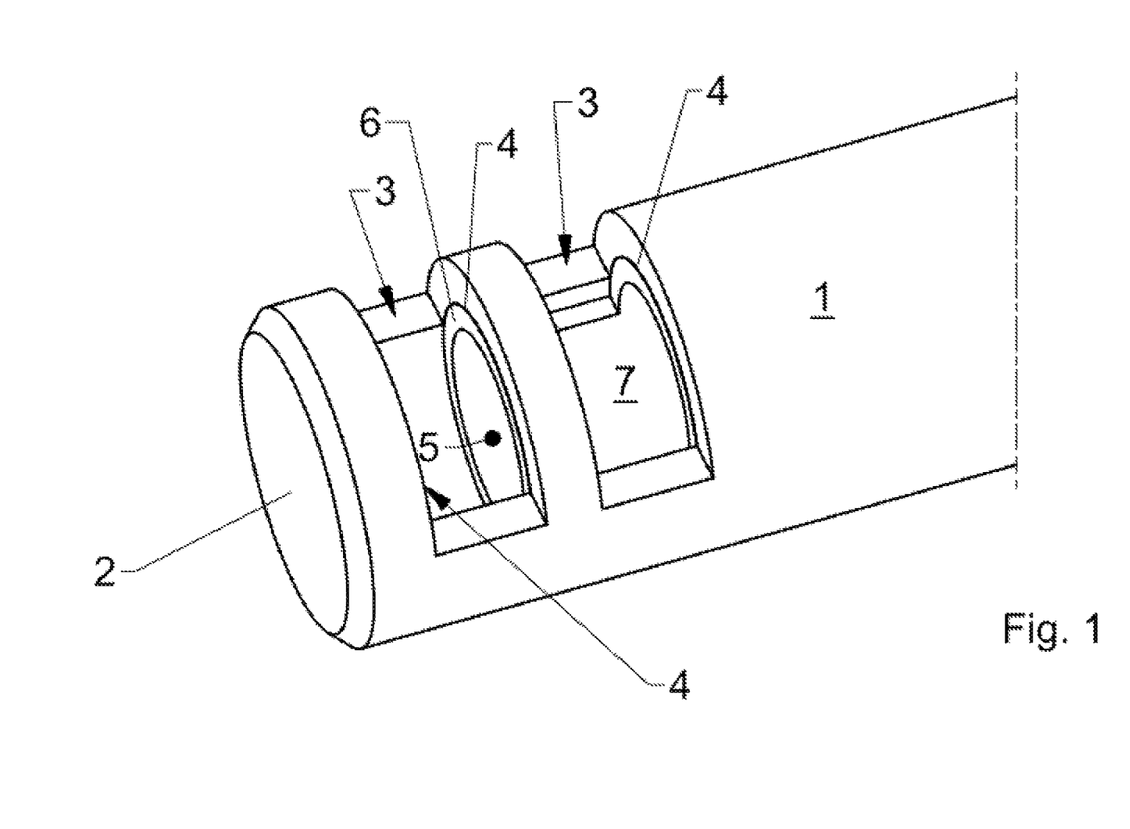
FIG. 1-6 partially show, in schematic views, one embodiment of a device according to the invention for cutting and suctioning tissue, wherein the figures show the movement profile of the inner tube in the outer tube, and the openings and cutting edges included in these positions.
Figure 2:
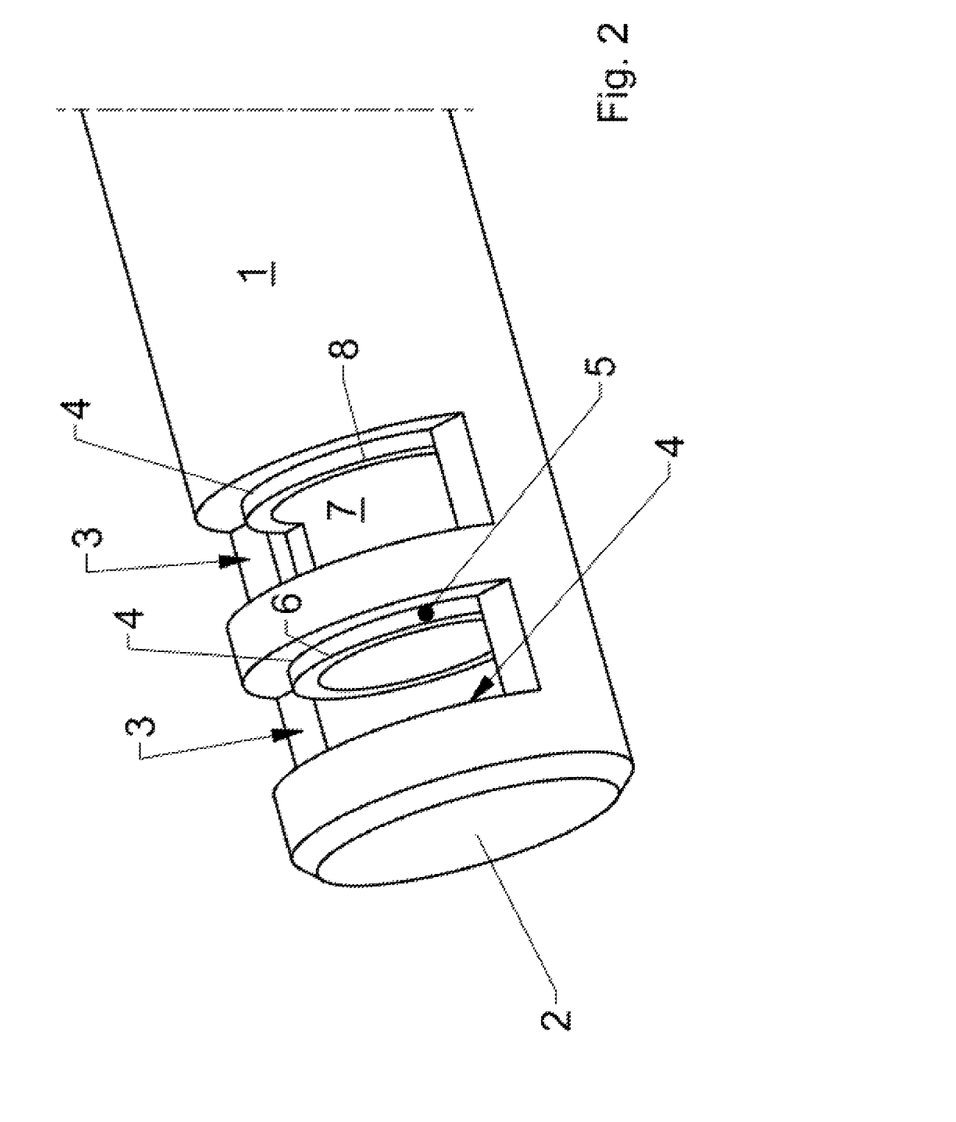
Figure 3:
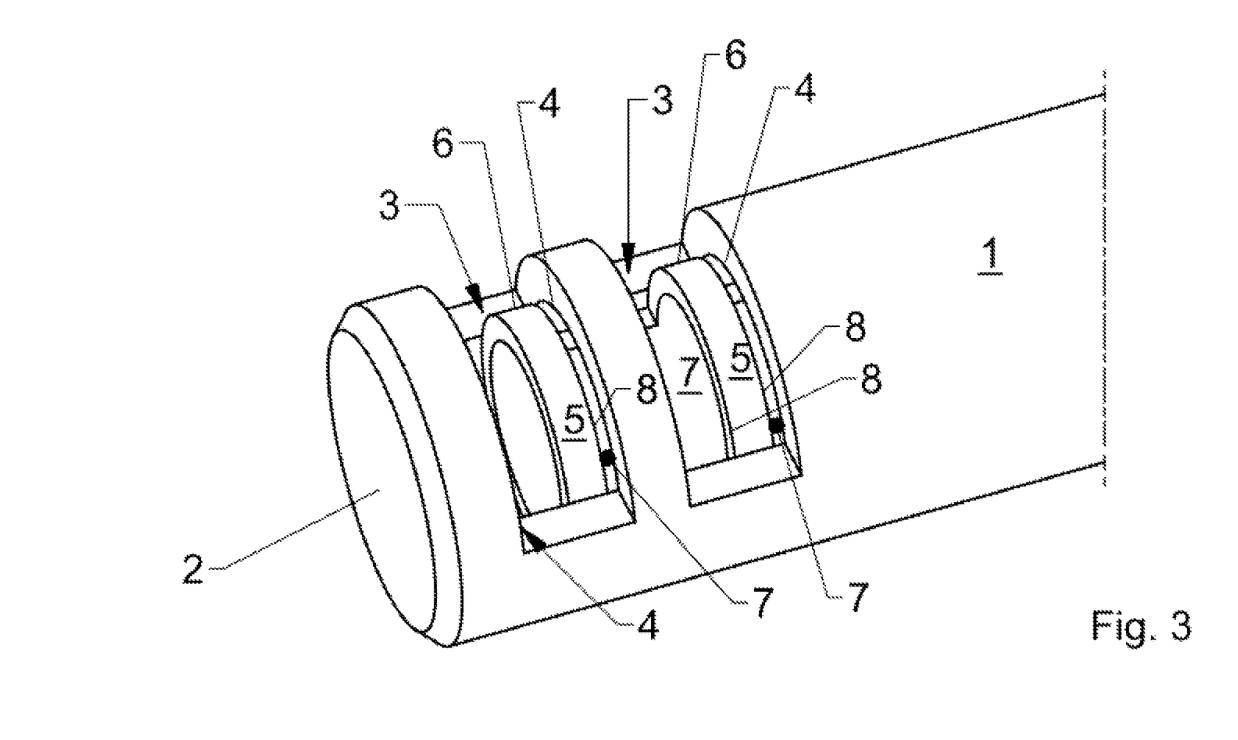
Figure 4:
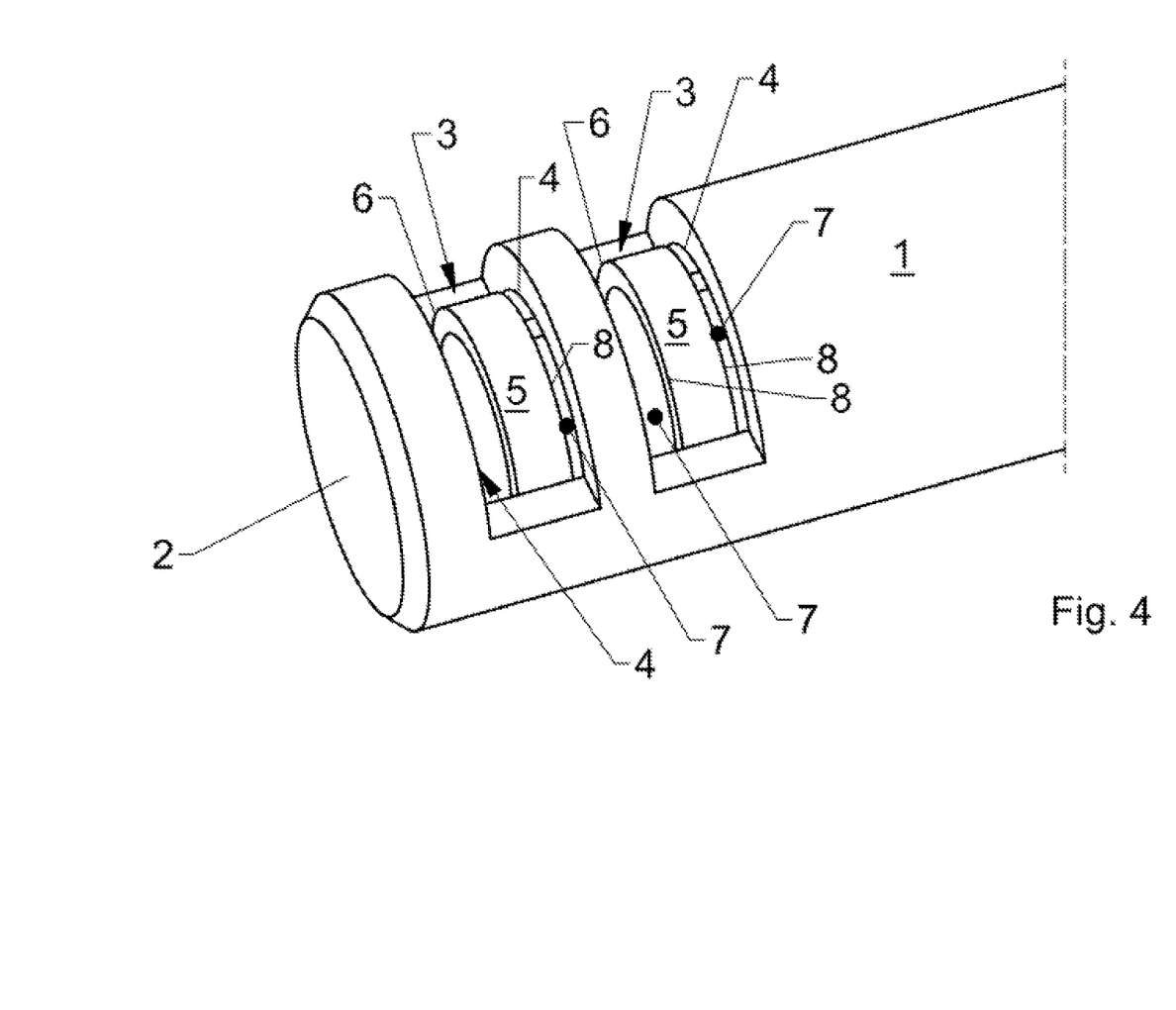
Figure 5:
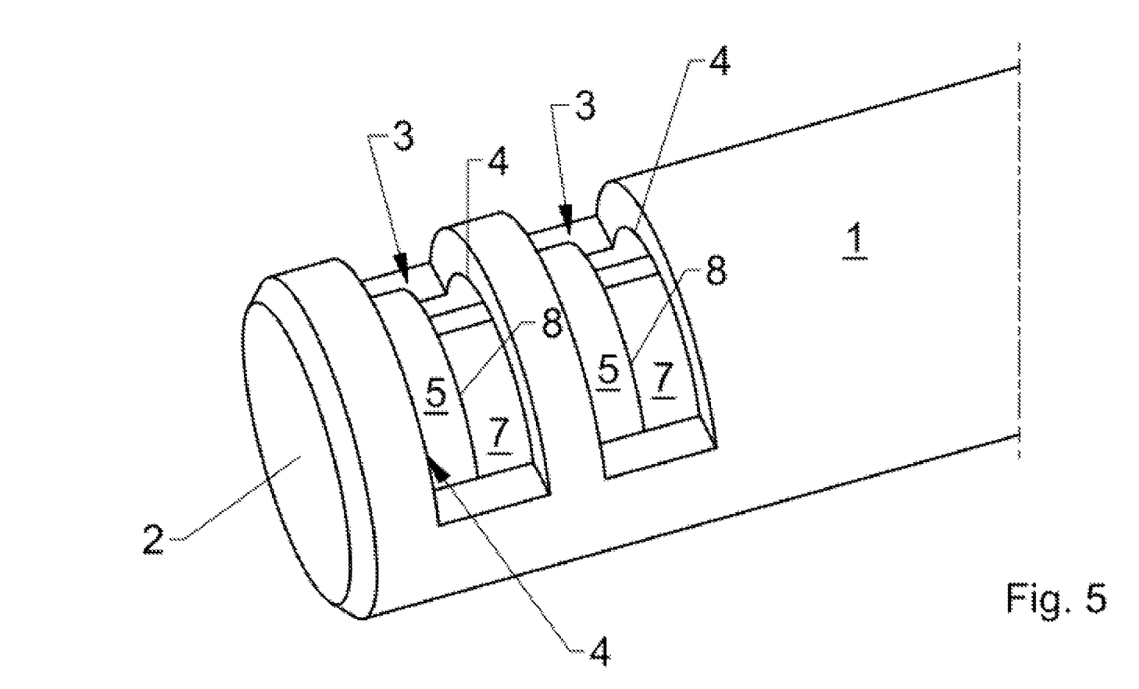
Figure 6:
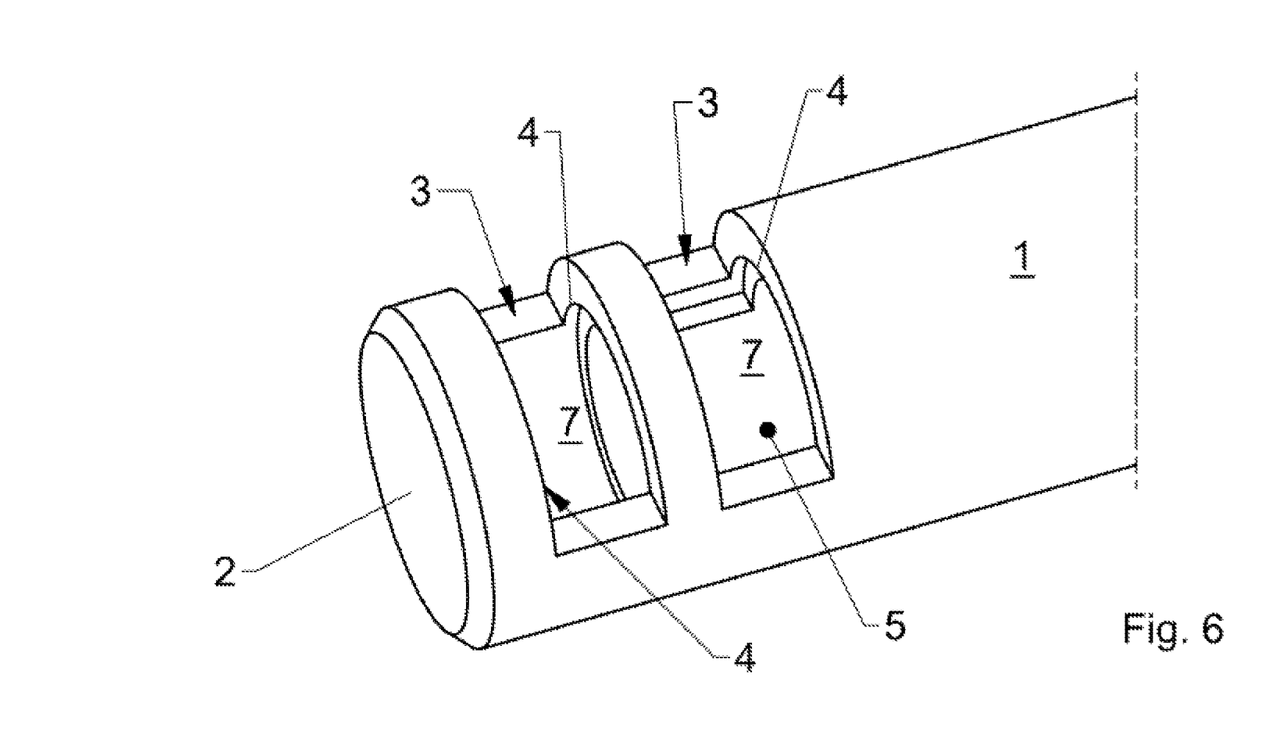
Figure 7:
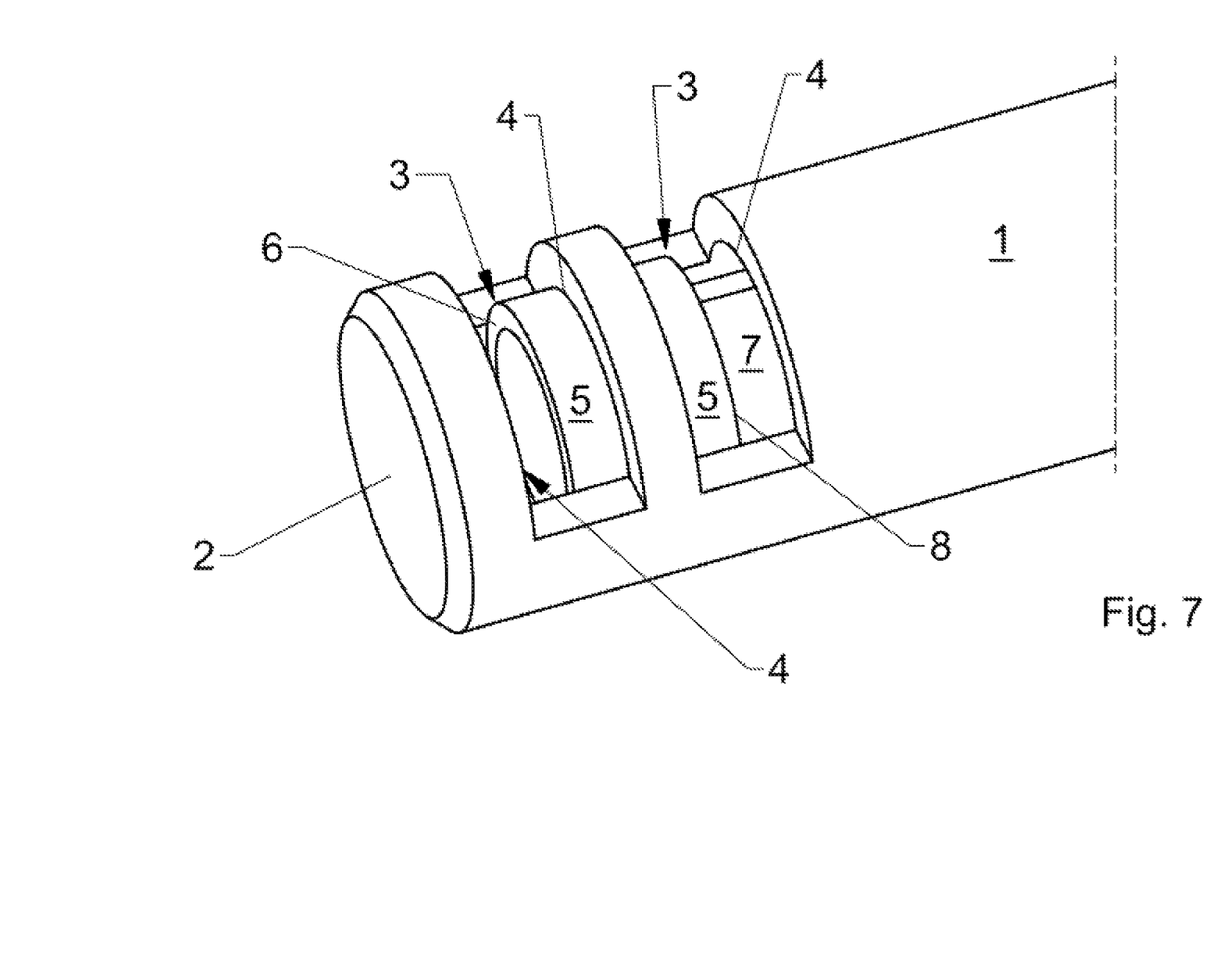
FIG. 7 shows a schematic top view of one variant of the device according to the invention, according to which the flow path directed into the inner tube is constant at every point in time of the movement profile.

Both with the provision of a single opening 7 in the inner tube 5 and with the provision of two openings 7 of the inner tube 5, these can be sized and positioned in such a manner that, when the inner tube 5 moves suitably inside the outer tube 1, the same cross-section of flow is always implemented, particularly when the one opening 3 in the outer tube 1 is open or closed and the other opening 3 in the outer tube 1 is closed or open. At this point, reference is made to the schematic illustration in FIG. 7. In a central position, therefore, the openings 3 in the outer tube 1 would each be half-closed and/or open according to the position of the cutting edges 8 of the inner tube 5 by means of the migration of the inner tube 5.

It is hereby noted at this point that the device according to the invention is merely illustrated schematically in the figures, particularly in order to show fundamental embodiments and the profile of movement. For reasons of clarity, no illustrations of details have been provided.

Finally, it is hereby noted that the embodiment described above merely serves as an exemplary explanation of the claimed teaching; however, the latter is not restricted to the embodiment.

LIST OF REFERENCE NUMBERS 1 outer tube
2 free end of 1
3 lateral opening of 1
4 inner cutting edge of 1
5 inner tube
6 outer cutting edge of 5
7 lateral openings of 5
8 additional outer cutting edges of 5

The invention claimed is:

1. An apparatus for cutting and aspirating tissue from the human body or animal body for application in vitrectomy, said apparatus comprising:
   an outer tube (1); and
   an inner tube (5), which can slide back and forth concentrically in the outer tube (1) with minimal play, wherein:
   the outer tube (1) is closed on a free end thereof and has a first lateral opening (3) near the free end and a similarly shaped second lateral opening (3) spaced apart from the first lateral opening so as to define there-between a closed portion of the outer tube (1), the first lateral opening (3) and the second lateral opening (3) each having at least one inner cutting edge (4), the closed portion having a length defined along a longitudinal axis of the outer tube (1);
   the inner tube (5) is open on a distal end (2) thereof and has an outer cutting edge (6) at that position;
   the at least one inner cutting edge (4) of each of the first and second lateral openings of the outer tube (1) and the outer cutting edge (6) at the distal end of the inner tube work (5) together in a cutting manner when the inner tube (5) is displaced; and
   the inner tube (5) has at least one lateral opening (7) near the distal end (2), the at least one lateral opening (7) having at least one further outer cutting edge (8) and a length defined along a longitudinal axis of the inner tube (5), the length of the at least one lateral opening (7) of the inner tube (5) being greater than the length of the closed portion defined between the first and second lateral openings (3) of the outer tube (1), the relative lengths of the at least one lateral opening (7) of the inner tube (5) and the closed portion of the outer tube (1) defining a constant cross-section of flow into the inner tube (5) at every position of the inner and outer tubes (5, 1) relative to one another.

2. An apparatus according to claim 1, wherein the at least one further outer cutting edge (8) of the at least one lateral opening (7) of the inner tube (5) comprises two outer cutting edges (8).

3. An apparatus according to claim 1, wherein:
   the at least one lateral opening (7) the inner tube (5) comprises at least two lateral openings (7) near the distal end of the inner tube (5), and
   the at least one further outer cutting edge (8) comprises at least three outer cutting edges (8) of the at least two lateral openings (7) of the inner tube (5).

4. An apparatus according to claim 3, wherein the at least three outer cutting edges (8) comprise four outer cutting edges (8) of the at least two lateral openings (7) of the inner tube (5).

5. An apparatus according to claim 1, wherein:
the first and second lateral openings (3) of the outer tube (1) and the at least one lateral opening (7) of the inner tube (5) are designed as slits which are parallel to each other, and
each of the at least one inner cutting edges (4) of the outer tube (1) and the at least one further outer cutting edge (8) of the inner tube (5) are parallel to each other.

6. An apparatus according to claim 1, wherein the at least one inner cutting edge (4) of each of the first lateral opening (3) and the second lateral opening (3) collectively comprise at least three inner cutting edges (4).

7. An apparatus according to claim 6, wherein the at least three inner cutting edges (4) comprise four inner cutting edges (4).

8. An apparatus according to claim 1, wherein the first and the second lateral openings (3) of the outer tube (1) and the at least one lateral opening (7) of the inner tube (5) are designed as slits which are parallel to each other and wherein the at least one inner cutting edge (4) of each of the first and the second lateral openings (3) of the outer tube (1) are each parallel to the at least one further outer cutting edge (8) of the at least one lateral opening (7) of the inner tube (5).

9. An apparatus according to claim 1, wherein each of the at least one inner cutting edges (4) of the outer tube (1) and the at least one further outer cutting edge (8) of the at least one lateral opening (7) of the inner tube (5) run transverse to the longitudinal axes of the inner and outer tubes (1, 5).

10. An apparatus according to claim 1, wherein each of the at least one inner cutting edges (4) of the outer tube (1) and the at least one further outer cutting edge (8) of the at least one lateral opening (7) of the inner tube (5) run diagonally to the longitudinal axes of the inner and outer tubes (1, 5).

11. An apparatus according to claim 1, wherein the outer cutting edges (6) and at least one further outer cutting edge (8) of the inner tube (5) have a different angle with respect to the longitudinal axis of the inner tube (5) than the each of the at least one inner cutting edges (4) of the outer tube (1).

12. An apparatus according to claim 1, wherein each of the at least one inner cutting edges (4) of the outer tube (1), the outer cutting edge (6) at the distal end of the inner tube (5), and the at least one further outer cutting edge (8) of the at least one lateral opening (7) of the inner tube (5) are designed as straight.

13. An apparatus according to claim 1, wherein each of the at least one inner cutting edges (4) of the outer tube (1), the outer cutting edge (6) at the distal end of the inner tube (5), and the at least one further outer cutting edge (8) of the at least one lateral opening (7) of the inner tube (5) are designed as at least one of curved, wavy, and beveled.

14. An apparatus according to claim 1, wherein cutting surfaces defined by the material thickness of the inner and outer tubes (1, 5) each extend from each of the at least one inner cutting edges (4) of the outer tube (1), the outer cutting edge (6) at the distal end of the inner tube (5), and the at least one further outer cutting edge (8) of the at least one lateral opening (7) of the inner tube (5).

15. An apparatus according to claim 14, wherein the cutting surfaces defined by the material thickness of the inner and outer tubes (1, 5) each extend and fall away outward from the each of the at least one inner cutting edges (4) of the outer tube (1), the outer cutting edge (6) at the distal end of the inner tube (5), and the at least one further outer cutting edge (8) of the at least one lateral opening (7) of the inner tube (5).

16. An apparatus according to claim 14, wherein the cutting surfaces defined by the material thickness of the inner and outer tubes (1,5) each extend and fall away inward from the each of the at least one inner cutting edges (4) of the outer tube (1), the outer cutting edge (6) at the distal end of the inner tube (5), and the at least one further outer cutting edge (8) of the at least one lateral opening (7) of the inner tube (5).

17. An apparatus according to claim 1, wherein at least one of the first lateral opening (3) or the second lateral opening (3) of the outer tube (1) and the at least one lateral opening (7) of the inner tube (5) are spaced apart from each other in an axial dimension.

18. An apparatus according to claim 1, wherein at least one of the first lateral opening (3) or the second lateral opening (3) of the outer tube (1) and the at least one lateral opening (7) of the inner tube (5) are arranged offset to each other with respect to a peripheral direction.

19. An apparatus according to claim 1, wherein the first and the second lateral openings (3) of the outer tube (1) have the same shape.

* * * * *

UNITED STATES PATENT AND TRADEMARK OFFICE
CERTIFICATE OF CORRECTION

| | | |
|---|---|---|
| PATENT NO. | : 9,668,918 B2 | Page 1 of 1 |
| APPLICATION NO. | : 13/880353 | |
| DATED | : June 6, 2017 | |
| INVENTOR(S) | : Geuder | |

It is certified that error appears in the above-identified patent and that said Letters Patent is hereby corrected as shown below:

In the Specification

<u>Column 7</u>
Line 36, "edges" should read --edge--

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*